United States Patent [19]
Barton et al.

[11] Patent Number: 5,760,704
[45] Date of Patent: Jun. 2, 1998

[54] PATIENT TRACKING SYSTEM FOR HOSPITAL EMERGENCY FACILITY

[75] Inventors: Giles L. Barton, Atlanta; D. Phillip Pope, Canton, both of Ga.

[73] Assignee: Expeditor Systems, Alpharetta, Ga.

[21] Appl. No.: 863,216

[22] Filed: Apr. 3, 1992

[51] Int. Cl.$^6$ ............................................. G06F 159/00
[52] U.S. Cl. ...................... 340/825.49; 340/286.07; 379/38; 345/168; 345/44
[58] Field of Search ..................... 340/825.49, 573, 340/286.07; 379/38; 705/2, 3; 345/168, 44, 902

[56] References Cited

U.S. PATENT DOCUMENTS

| | | | |
|---|---|---|---|
| 2,910,680 | 10/1959 | McLain | 340/311 |
| 3,577,124 | 5/1971 | Kobayashi | 340/153 |
| 3,599,200 | 8/1971 | Bunting | 340/286 |
| 3,651,512 | 3/1972 | Summers | 340/325 |
| 3,962,698 | 6/1976 | Hunt et al. | 340/286 |
| 4,225,852 | 9/1980 | Waters et al. | 340/286.07 |
| 4,237,344 | 12/1980 | Moore | 379/38 |
| 4,418,334 | 11/1983 | Burnett | 340/286.07 |
| 4,725,694 | 2/1988 | Auer et al. | 379/96 |
| 4,745,404 | 5/1988 | Kallenberg | 340/752 |
| 4,803,625 | 2/1989 | Fu et al. | 364/413.02 |
| 4,851,811 | 7/1989 | Vallat et al. | 340/326 |
| 4,884,068 | 11/1989 | Matheny et al. | 340/707 |
| 4,967,195 | 10/1990 | Shipley | 340/825.52 |
| 5,072,383 | 12/1991 | Brimm et al. | 364/413.02 |
| 5,101,476 | 3/1992 | Kukla | 364/413.02 |
| 5,103,204 | 4/1992 | Hartman | 340/286.07 |

*Primary Examiner*—Brian Zimmerman
*Assistant Examiner*—William H. Wilson, Jr.
*Attorney, Agent, or Firm*—Jones & Askew, LLP

[57] ABSTRACT

An electronic patient tracking system for use in a hospital, particularly a hospital emergency room facility. A plurality of patient tracking modules are provided, each of which includes a multi-character display for indicating patient name and patient complaint as well as an indicator of attending physician and nurse. Illuminated color coded switches are used to indicate the placement of orders for work to be done. The system provides automatic timeouts if the order is not completed, as evidenced by subsequent operation of the switch, within a predetermined period of time and changes the lamp status to an alarm condition, such as flashing with a particular cadence. The system allows local entry of data and setting of order indicators as well as the control of these elements from a host computer system of the hospital in which the device is used. It also provides for a complete transfer of identification information and order status among patient modules when a patient is moved between rooms associated with particular modules.

4 Claims, 6 Drawing Sheets

PATIENT TRACKING SYSTEM FOR HOSPITAL EMERGENCY FACILITY

TECHNICAL FIELD

The present invention relates to the field of patient tracking apparatus for use in hospitals, particularly in hospital emergency room facilities. More particularly, it implements electronic handling and manipulation of information kept on a hospital patient chart.

BACKGROUND OF THE INVENTION

The present invention is an electronic patient tracking system for use in a hospital. While it has uses in virtually any hospital environment, it was principally designed to be used in a hospital emergency room facility. As will be appreciated from the description below, a number of features of the present invention, and particular preferred forms thereof, are particularly suited for the environment and needs of an emergency room facility.

Modern hospitals, at least in the United States of America, have a widespread reputation for requiring extensive amounts of information from patients prior to provision of outpatient treatment or admission to a hospital. While the need for such information is often not appreciated by the patient, obtaining information is serious and important work in a modern hospital. The facility must know the correct identity of the person, the correct identity of the attending physician, and the reason the patient is admitted to the hospital. As the culture in the U.S.A. has become more litigious, hospitals must be more and more careful as they are often the targets of professional negligence claims, some of which arise from incorrect information being recorded about a patient.

A hospital emergency room facility is somewhat peculiar in that patients are often brought into the facility with serious life threatening injuries or ailments. Many emergency treatment situations are ones for which there is little or no opportunity to obtain routine information about the patient. When a newly arrived patient has a serious and immediately life threatening situation, treatment will often begin prior to the formalities of admission or even complete identification of the patient.

Physicians and nurses working in emergency room environments are often under considerable stress. The tracking of patient information and orders for X-rays, medication, and the like can be crucial at the outset. As in most high stress situations, the provision and display of important information should be both prominent and simple.

Furthermore, in hospital emergency facilities, it is often desirable to switch patients among various rooms as the patient's needs and condition change and as other patients having greater need of particular facilities arrive. It is important that correct information identifying the patient and his or her condition follow the patient as he or she moves through the hospital. While this is true in virtually all situations in a hospital, it is particularly important in an emergency room facility since the patients are often unconscious or incommunicative as to their identity, and often receive their most vital treatment early in their stay before the staff has become familiar with the identities of different individuals.

In many situations, a number of physicians orders are made with respect to a patient's treatment during the first hour of the patient's stay in the facility. For example, once victims of an automobile wreck are stabilized, a physician will often order X-rays. Furthermore, laboratory work is often required early in the patient's stay.

Various electronic communications systems annunciators and doctors registers have been designed for and used in hospitals. Such communications systems have generally been designed to communicate among various facilities in a hospital, to provide particularized nurse or physician call signals, or to provide silent paging systems and information identifying particular physicians who are in the hospital at any given time.

For example, U.S. Pat. No. 4,967,195 to Shipley shows a multi-drop audio communications system for use in a hospital that also includes conventional nurse call and patient emergency switches. Requests for nursing assistance, including those made for patient shower facilities and other potentially dangerous areas, are communicated over multi-drop buses to the nursing station via a central controller. The conventional dome light outside the patient's room is activated and the nursing station is also alerted that the patient's request for assistance. The system of the Shipley '195 patent also provides prioritizing of verbal communication calls among hospital facilities. There is a basic architectural similarity between the system disclosed in Shipley '195 and the preferred embodiment of the present invention in that a central controller polls a plurality of remote controller devices to which peripheral devices are attached and all communication among different remote controllers are effected via packets passed through the central controller.

The prior art has also provided plural lighted indicators associated on a one-to-one basis with patients in particular rooms that indicate particular patient requests. For example, U.S. Pat. No. 2,910,680 to McLain shows a patient-to-nursing station annunciator system wherein each patient room is provided with a keyboard having a plurality of keys that may be depressed in order to activate particular lights at a nurses station indicating, for example, that the patient requests the nurse's assistance, needs water, or to have other services performed. Setting of the lamps is controlled at the patient's room and is also cleared there. Thus, the system of the McLain '680 patent provides only a silent annunciator providing a visual indication of a patient service request.

As far as is known to the inventors of the present invention, heretofore there has been no electronic patient tracking system that effectively implements the basics of an electronic patient chart in a hospital environment.

SUMMARY OF THE INVENTION

The present invention is a hospital patient tracking system that provides an electronically generated visible display of the most important elements of a patient's chart. In particular, it provides collections of patient tracking modules in which patient identification information such as the patient's name, the particular condition for which the patient is being treated, and identification of attending physician and nurse are visually displayed on a module associated with the room in which the patient is physically located. Additionally, each patient tracking module has a plurality of selectively actuable visual indicators, preferably embodied by incandescent lamps, which indicate that certain orders have been placed by the attending physician. In the preferred form of the present invention, each of the order lamps is integrally formed with a switch that activates the lamp at the patient tracking module. In other words, the preferred implementation for the visible order indicators are lighted switches where operation of the switch controls turning its associated lamp on and off.

In the preferred form of the present invention a central controller monitors the placement of particular types of orders by noting the activation of an order lamp and includes timing apparatus which checks to see if each order has been fulfilled within a predetermined period of time associated with the particular type of order. A second activation of the switch associated with the order lamp is the event that tells the central controller that the order has been filled. This is accomplished when a nurse or attending physician operates the switch associated with the order lamp a second time to indicate that the task has been performed.

In the preferred embodiment the central controller will place the lamp in an alarm state if a predetermined period of time elapses and it has received no indication that the order has been fulfilled. The preferred form of the alarm state is a flashing condition on the lamp. In its most preferred form, a second alarm state is also generated which is manifested as a more rapid flashing pattern.

In preferred forms of the present invention, at least a subset of the order lamps and associated controlling switches are reproduced at each patient room. Therefore, a member of the hospital staff can deactivate the order lamp when the services requested by the order have been performed. For example, if the attending physician has ordered certain types of blood tests to be performed on the patient, the nurse or technician who draws the patient's blood for the laboratory can deactivate the laboratory order lamp by pressing a corresponding laboratory order switch in the patient's room. This deactivates the lamp at both the patient room and the patient tracking module, which is normally located in a plurality of patient tracking modules at a nurses station.

Thus, it will be seen that each patient tracking module presents a compact electronically provided visual display of the basics of a patient's chart. It shows the patient name and a brief description of the patient's complaint. It indicates the attending physician, responsible nurse and the status of any unfilled orders made by the attending physician.

The present invention arranges the patient tracking modules in clusters wherein each cluster is controlled by one or more cluster controllers that control various devices within each patient tracking module that is a member of the cluster. A central controller is connected, preferably via a multi-drop serial link, to each of the cluster controllers. A keyboard or other terminal device is provided to facilitate entry of patient identification information, including the name, patient's medical problem, and attending nurse and physician. In the preferred embodiment a keyboard facility is provided for each pair of clusters of patient tracking modules, although replication of the keyboard is dictated by space and cost constraints and the facility's experience and the need for the ability to access more than one keyboard at the same time.

In the preferred form of the present invention, a second serial link is provided from the central controller of the present invention to a host computer for the hospital facility. This allows electronic routing of patient identification information directly to the patient tracking system of the present invention if the hospital and the patient's condition allow collection of this information at the time of admission. For example, if a trauma patient is admitted to an emergency room facility under the care of a particular physician and a relative of the patient provides the patient's name at an admissions desk, the attendant taking the relevant information at the attendants desk can assign the patient to a particular room in the emergency facility and instruct the computer to enter the record. The record is stored, under control of the program controlling the hospital's host computer system, in appropriate records for the hospital computer system. Additionally, the host program need be modified only to provide a burst of data in a particular format through a conventional serial link, preferably RS-232, to the central controller of the patient tracking system of the present invention. A simple set of ASCII commands is used to allow the host to provide instructions to the central controller in this manner. When this feature is used, the hospital host computer picks up the room assignment and routes the patient identification information and, if provided, any previously provided physician's orders, to the central controller of the patient tracking system. The central controller then routes this information to the appropriate cluster controller in order to have it displayed immediately in a patient tracking module associated with a room to which the patient has been assigned. Therefore, in the preferred form of the present invention initiation of an electronic chart and a patient tracking module may be made either at a keyboard or terminal that is part of the patient tracking system, per se, or via information provided from an external host computer, normally the central computer system serving the hospital facility at which the patient tracking system is located.

Furthermore, in preferred forms of the present invention a simple set of key strokes may be used to transfer all of the patient identification and order information from the module associated with one room to the patient tracking module associated with another room when the patient is physically moved within the hospital. This operation likewise controls the status of the replicated order indicator lights at the new destination room and terminates operation of those lights in the room being vacated.

Thus, it is an object of the present invention to provide a plurality of basic electronic patient charts at a nursing station or other central facility where a group of patients are being treated. It is also an object of the present invention to provide such an electronic chart that provides textual information on the identification of the patient and his or her medical condition, the attending physician, and a simple, highly visible, color coded indication of the status of particular orders.

It is a further object of the present invention to provide such a plurality of patient tracking modules in which automatic event timers place order indicators in alarm states if a predetermined period of time elapses without fulfillment of particular orders.

It is still a further object of the present invention to provide such an electronic patient tracking system that is physically arranged with a central controller and a plurality of cluster controllers, each of which controls an associated cluster of patient tracking modules. This provides expandability of the system by the addition of more cluster controllers. Since the association of each patient tracking module with a physical room is made only on a logical basis, the system can be reconfigured to designate certain patient tracking modules as being associated with certain physical rooms or other locations within the facility as the needs of the hospital evolve.

It is still a further object of the present invention to provide an electronic patient tracking system for a hospital where order status indicators may be selectively activated and deactivated from a plurality of locations, including a central location such as a nurses station, individual patient locations such as patient rooms, and via communication with a central host computer of the hospital in which the patient tracking system is located.

That the present invention meets these objects will be appreciated from the detailed description of the preferred embodiment to follow.

DETAILED DESCRIPTION OF THE PREFERRED EMBODIMENT

Figure 1:
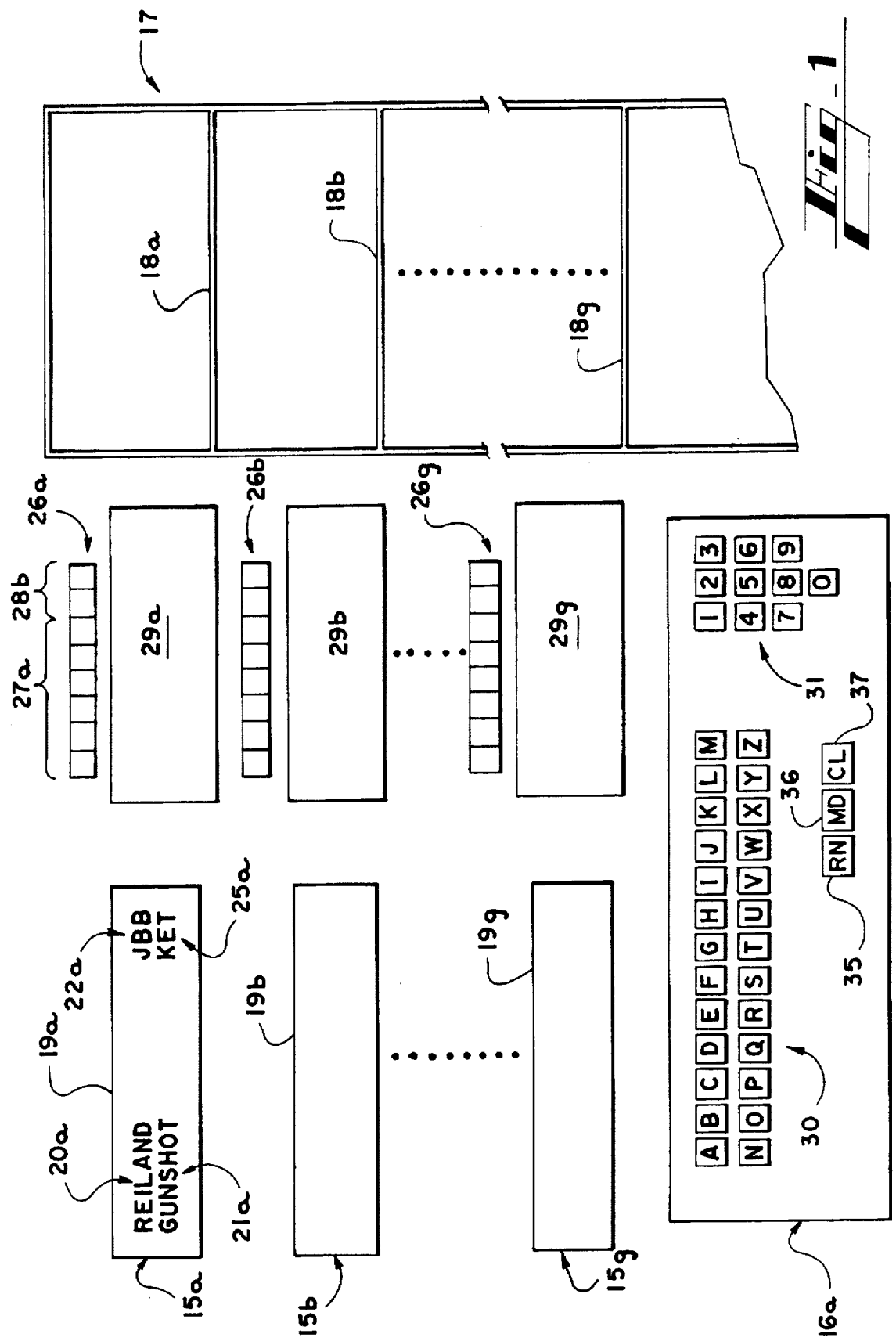
FIG. 1 is a partial pictorial view of the physical arrangement of displays and keys, lamps and keyboards of the preferred embodiment of the present invention.

Turning now to the drawings in which like numerals reference like parts, the preferred embodiment of the present invention will now be described. FIG. 1 shows a graphic representation of a portion of the preferred embodiment of the present invention in a front elevational view.

Three of the seven patient tracking modules 15a–15g, which seven modules constitute a patient tracking module cluster, are shown in FIG. 1. Below the patient tracking modules is an alphanumeric console keyboard 16a.

The preferred embodiment includes a rack of physical chart pigeon holes generally indicated at 17. This provides a plurality of shelves 18a–18g associated on a one-to-one basis with each of patient tracking modules 15. Thus, in its preferred form a holder for a conventional patient chart on a clipboard is provided next to the electronic patient tracking module associated with the patient whose chart will be placed on the shelf.

Patient tracking module 15a includes a multi-character display 19a. In the preferred embodiment, the multi-character displays 19 are preferably embodied by 2×20 character vacuum fluorescent dot matrix display devices manufactured by Industrial Electronic Engineers of Van Nuys, Calif. These displays are logically divided by the central controller's firmware into four fields. The first is a 15 character patient name field indicated at 20a. Secondly, a 15 character patient condition field is shown as 21a in display 19a. A three character attending physician field 22a appears in the upper right hand corner of display 19a and a three character attending nurse field 25a is in the lower right hand corner. Thus, it will be appreciated that in the example shown for patient tracking module 15, a patient named Reiland has been assigned to the room associated with patient tracking module 15a. Mr. Reiland is suffering from a gun shot wound as indicated by the contents of field 21a. The attending physician has initials "JBB" and the attending nurse has initials "KET". Naturally, numerical designations or alphanumeric designations may be used for indicating the attending nurse or physician in fields 22 and 25.

Patient tracking module 15a also includes a row of eight momentary key switches. The six left hand members of the set of keys 26a are indicated by bracket 27a. Each of these has an associated lamp behind the key and a color coded lens over the lamp. The two right hand keys indicated at 28b are non-illuminated. These are move and enter keys, the functions of which are described in greater detail hereinbelow.

Also associated with each patient tracking module is a writing surface 29. This is simply a small smooth white board area upon which notes may be written in erasable markers for the convenience of the staff.

Keyboard 16a includes an array of 26 keys, indicated at 30, for entering characters of the Roman alphabet and a numeric keypad shown at 31. Additionally, three dedicated function keys 35–37 are included near the bottom of keyboard 16a. Key 35 labeled "RN" is a key that is operated when entering an attending nurse identifier. Key 36, labeled "MD" is operated to indicate that the information should be placed in an attending physician field 22, and clear key 37 clears a previously started keystroke sequence.

Before moving on to other details of the preferred embodiment it should be appreciated that illuminated keys 27a each represent a particular type of order. When illuminated they indicate that an unfulfilled order of the type designated by the key location and color has been ordered by the physician. Thus, it may be seen that a physician or nurse quickly glancing at patient tracking module 15a can immediately ascertain that patient Reiland is suffering from a gun shot wound, can identify the physician and nurse in charge of the patient, and inspection of lighted keys 27a will indicate what orders of physician JBB remain to be filled. If any of the lamp indicators are flashing, this condition will tell the observer that the order has been pending for what the system defines as a significant period of time and needs to be attended to promptly. Any notes that an attendant may have left on writing surface 29a are visible, and an inspection of the patient's conventional chart may be made by retrieving same from shelf 18a.

In order to avoid a cluttered drawing and unnecessary detail, only portions of the preferred embodiment have been illustrated in FIG. 1. It should be understood that the preferred embodiment of the present invention was originally constructed having 42 patient tracking modules for an emergency room facility at a particular hospital. These were arranged as six clusters with seven patient tracking modules in each cluster. A keyboard of the type indicated as keyboard 16a was associated with each pair of clusters. Physically the patient tracking modules were arranged with a column of seven modules above the keyboard, as indicated in FIG. 1, and a second cluster of modules below the keyboard. This combination of 14 patient tracking modules with a alphanumeric keyboard was replicated three times, side by side, at a nurses station.

Generally speaking, it will be apparent from the description of the preferred embodiment to follow that eight patient tracking modules can be associated with each cluster of the preferred embodiment. Furthermore, only one alphanumeric keyboard is required and these are replicated for the convenience of the users so as not to cause a bottleneck for the entry of doctor and nurse identification information.

Naturally, the details of patient tracking modules per cluster and the association of keyboards with two or more clusters are merely construction details of the preferred embodiment and should not be viewed as limitations on the scope of the present invention.

Figure 2:
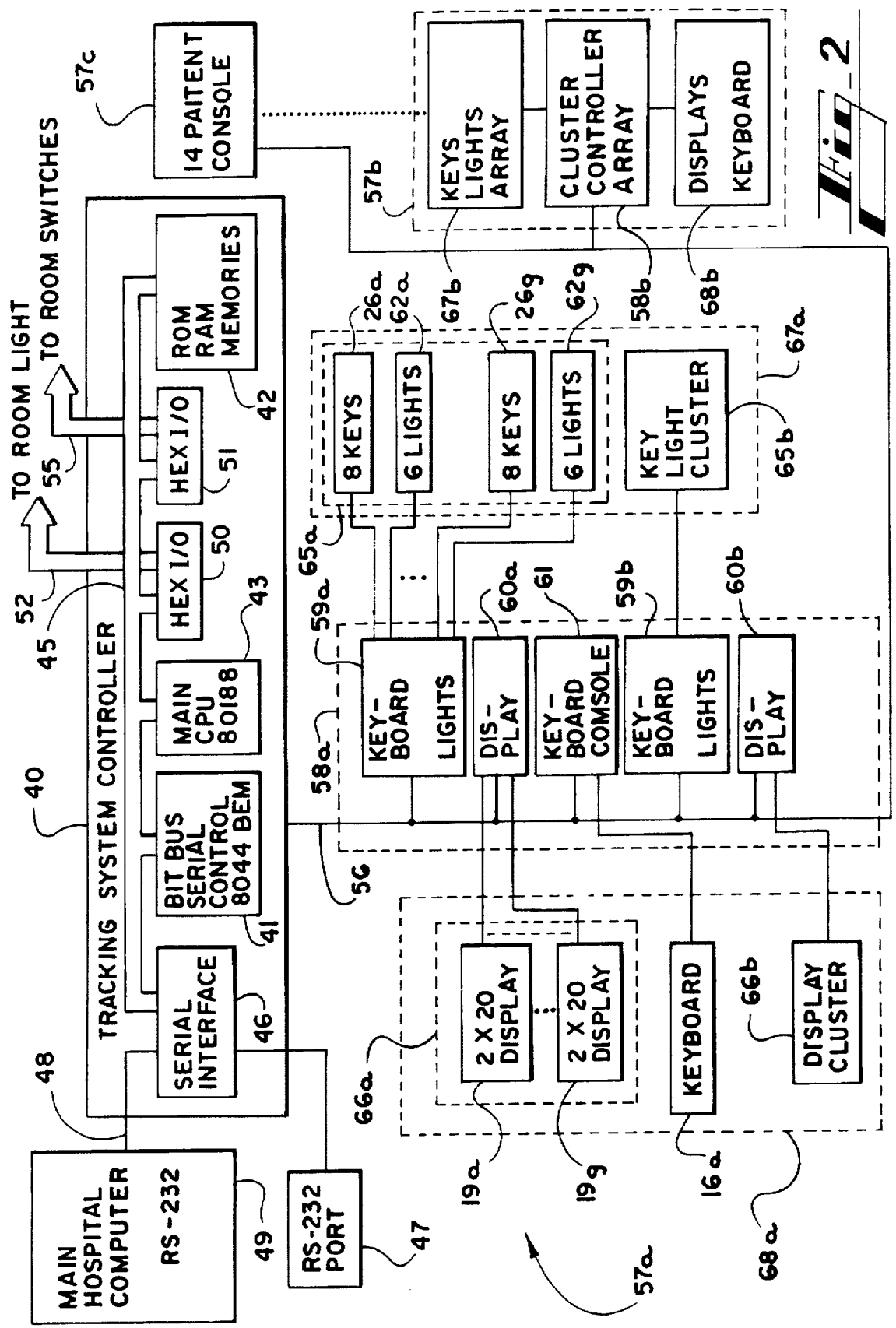
FIG. 2 is a block diagram of the preferred embodiment of the patient tracking system of the present invention.

Turning next to FIG. 2, a block diagram of the preferred embodiment is shown. The main intelligence of central controller 40 is implemented by an Intel type 80188 microprocessor. The central controller 40 controls all communications among components of the system of the preferred embodiment. It has a master/slave relationship with the cluster controllers, described more fully hereinbelow. Communication with the cluster controllers is implemented by a type 8044BEM one chip microcomputer 41 manufactured by Intel Corporation which includes Intel's proprietary Bitbus serial protocol control. Those skilled in the art of digital design will recognize that Intel's Bitbus protocol is a packetized serial communications protocol supported by a variety of Intel products. Details of the protocol are well documented in literature published by Intel Corporation. Of course, other data communications protocols could be used to construct embodiments of the present invention.

Central controller 40 also includes read only memory and random access memory devices indicated at 42 in FIG. 2. The read only memory portions store firmware that controls the operation of the controller as described in more detail hereinbelow. Random access memory is used to store a number of current tables and status lists for various devices in the system. CPU 43, Bitbus controller 41, and memories 42, together with other devices within central controller 40 communicate via a plurality of buses generally indicated at 45. A serial interface shown as 46 is connected to a patient tracking system external RS-232 port 47. This port is used to attach a diagnostic device to the system for monitoring system performance, tracking errors and other similar functions. Normally, either an on-site terminal will be attached to perform these functions or a modem will be connected to port 47 for remote analysis of system performance. A second RS-232 link 48 connects the main hospital computer shown as 49 on FIG. 2, to central controller 40.

Collections hex I/O chips are shown as 50 and 51 within central controller 40. These drive, respectively, a plurality of lines 52 that drive replicated order lights in the patient rooms and lines 55 that are connected to the associated switches on the order lights in the patient rooms. Thus, it is via lines 52 and 55 that central controller 40 controls the status of the replicated order lights in the patient rooms and detects operation of the switches at the patient rooms. Furthermore, it should be appreciated that any patient, doctor or nurse identification information to be displayed in one of displays 15 (FIG. 1) as well as any physician's orders that will activate the order lamps associated with key set 27 will be provided over serial link 48 when entered at the main hospital host computer 49. It will be readily appreciated that the embodiments of the present invention may be used quite effectively without connection to the hospital host computer 49 but that it is preferred to provide this link as a way of entering data for display into the patient tracking modules.

Central controller 40 communicates with the rest of the patient tracking system of the preferred embodiment via multi-drop Bitbus serial link 56. Serial link 56 is connected to three 14 patient consoles 57a–57c shown in FIG. 2. The 14 patient console 57a is shown in greater detail than the others to help in understanding of the architecture of the preferred embodiment. A plurality of five cluster controllers, collectively surrounded by dashed line 58a are the console controllers for one vertical panel. Each 14 patient console contains two clusters, each cluster having seven patient tracking modules.

Keyboard and lights cluster controller 59a controls key sets 26a–26g which are the eight key sets shown in FIG. 1. This cluster controller also controls seven sets of six order lamps each designated as 62a–62g. Collectively, these constitute a cluster 65a of keys and lights. A second keyboard and lights cluster controller 59b controls a second cluster of keys and lights 65b.

On the left hand side of FIG. 2, multi-character displays 19a–19g, which are displays 19 shown on FIG. 1, constitute a cluster 66a of the multi-character displays. Display cluster 66a is controlled by display cluster controller 60a. Similarly, an identical seven display cluster 66b is controlled by display cluster controller 60b. A keyboard console cluster controller 61 controls communication with keyboard 16a, which is also shown in FIG. 1.

The collection of two key and light clusters 65a and 65b are surrounded by dashed line 67a and thus constitute a cluster pair which forms the keys and lights for a 14 patient console. An identical set is shown as 67b within 14 patient console 57b in the drawing figure. The pair of display clusters 66a and 66b coupled with keyboard 16a is shown as surrounded by dashed line 68a in FIG. 2. Identical devices appear within the block labeled 68b within 14 patient console 57b. It should thus be understood that block 57c represents a replication of all of the elements shown within dashed lines 58a, 67a, and 68a.

The basic physical units of the patient tracking system of the preferred embodiment are the central controller 40 and cluster controllers 59, 60 and 61. Keyboard 16a is logically defined as providing entry of data into display clusters 66a and 66b in the preferred embodiment. However, it will be understood from the description of operation of the preferred embodiment provided below that this is a matter of design choice and a single keyboard could be used to provide entry of data into all of the displays of the preferred embodiment. Also, additional keyboards could be used wherein each keyboard serviced a smaller set of patient tracking modules, such as a single cluster rather than two clusters as is the case with the preferred embodiment.

Figure 3:
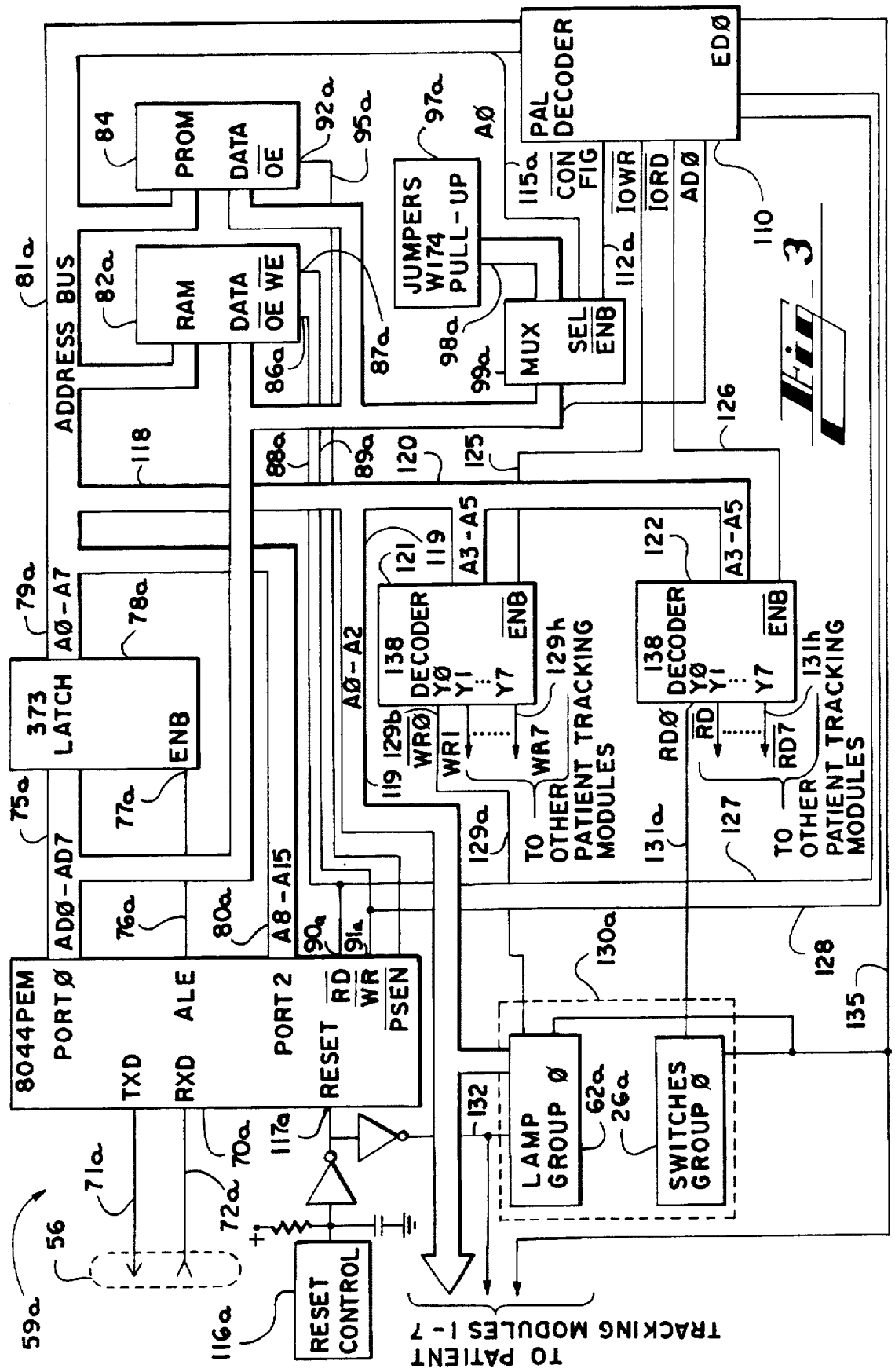
FIG. 3 is a partially schematic, partially block diagram of the preferred embodiment of the keyboard and visual indicator cluster controller used in the preferred embodiment.

The balance of the drawing figures show details of implementation of the device as illustrated on FIG. 2. FIG. 3 shows the preferred embodiment of keyboard and lights cluster controller 59a. It should be understood that the structure of all six of the keyboard and lights cluster controllers used the preferred embodiment are identical to that illustrated in FIG. 3. Also, it will become apparent that there is architectural similarity among all of the cluster controllers used in the preferred embodiment.

The intelligence and control of functions for keyboard and lights cluster controller 59a resides in an Intel type 8044BEM one chip microcomputer 70a. Those skilled in the art will recognize this part designation as a member of the MCS-51 microcomputer family made by Intel. In particular, this is a version of a type 8051 one chip microcomputer that includes support for communication via the Bitbus serial protocol over lines 71a and 72a. These are, respectively, the transmit data line and receive data line for the Bitbus serial protocol. Together they are attached as one drop of multi-drop serial link 56, as indicated in FIG. 3. As is conventional with members of the MCS-51 family, port 0 of the microcomputer is used as a combined address and data bus indicated as 75a. The low order address byte is put out on bus 75a during addressing of an external device and is latched, in response to an address latch enable signal on line 76a, into a type 373 latch 78a. The ALE signal on 76a is connected to enable input 77a of latch 78a. Thus, the latched outputs from latch 78a appear as the low order of address lines at 79a and are combined with the output from port 2 of microcomputer 70a. The port 2 output appears on sub-bus 80a, and is combined with sub-bus 79a to provide 16 bit address bus 81a.

Once the low order address bits are stored by latch 78a, bus 75a is used as the data bus. Address bus 81a and data bus 75a are connected to random access memory 82a and programmable read only memory 84. RAM 82a has negated output enable and write enable inputs 86a and 87a, respectively, that are connected by lines 88a and 89a to negated read enable (RD) output 90a and write enable (WR) output 91a in a conventional manner. Similarly, read only memory 84 has a negated output enable input 92a that is connected via line 95a to a program store enable output (PSEN) of microcomputer 70a. Thus, it will be understood that read only memory 84 contains program instructions constituting the firmware program driving microcomputer 70a and thus, controlling the operation of cluster controller 59a illustrated in FIG. 3.

A set of jumpers with pull-up resistors, indicated by block 97a, are provided on lines 98a to the inputs to a multiplexer 99a. PAL decoder 110 decodes a negated configuration signal (CONFIG) that takes line 112a into an active low condition, connecting the output of multiplexer 99a on to data bus 75a. A tap from the lowest order address line appears on line 115a and is connected to the select input of multiplexer 99a. Thus, when power is first turned on or a reset occurs, microcomputer 70a accesses a particular memory address that is decoded by PAL decoder 110 as the address for configuration information, which in turn manifests itself by line 112a going active low. The state of a first set of jumpers 97a is read. Subsequently, the microcomputer fetches an instruction for the same address incremented by one, which manifests itself as line 115a going from low to high. This reads the state of the balance of jumpers 97a. The jumpers 97a are configured in a conventional manner to define the logical address of cluster controller 59a and to provide information as to logical location of the patient tracking modules that are connected to the cluster. Resets are effected by a conventional reset control chip 116a which detects variations in line voltage and the like and applies a pulse of appropriate duration and polarity to reset input 117a of microcomputer 70a to cause the processor to reset, read its configuration jumpers 97a, and recommence operation.

Figure 5:
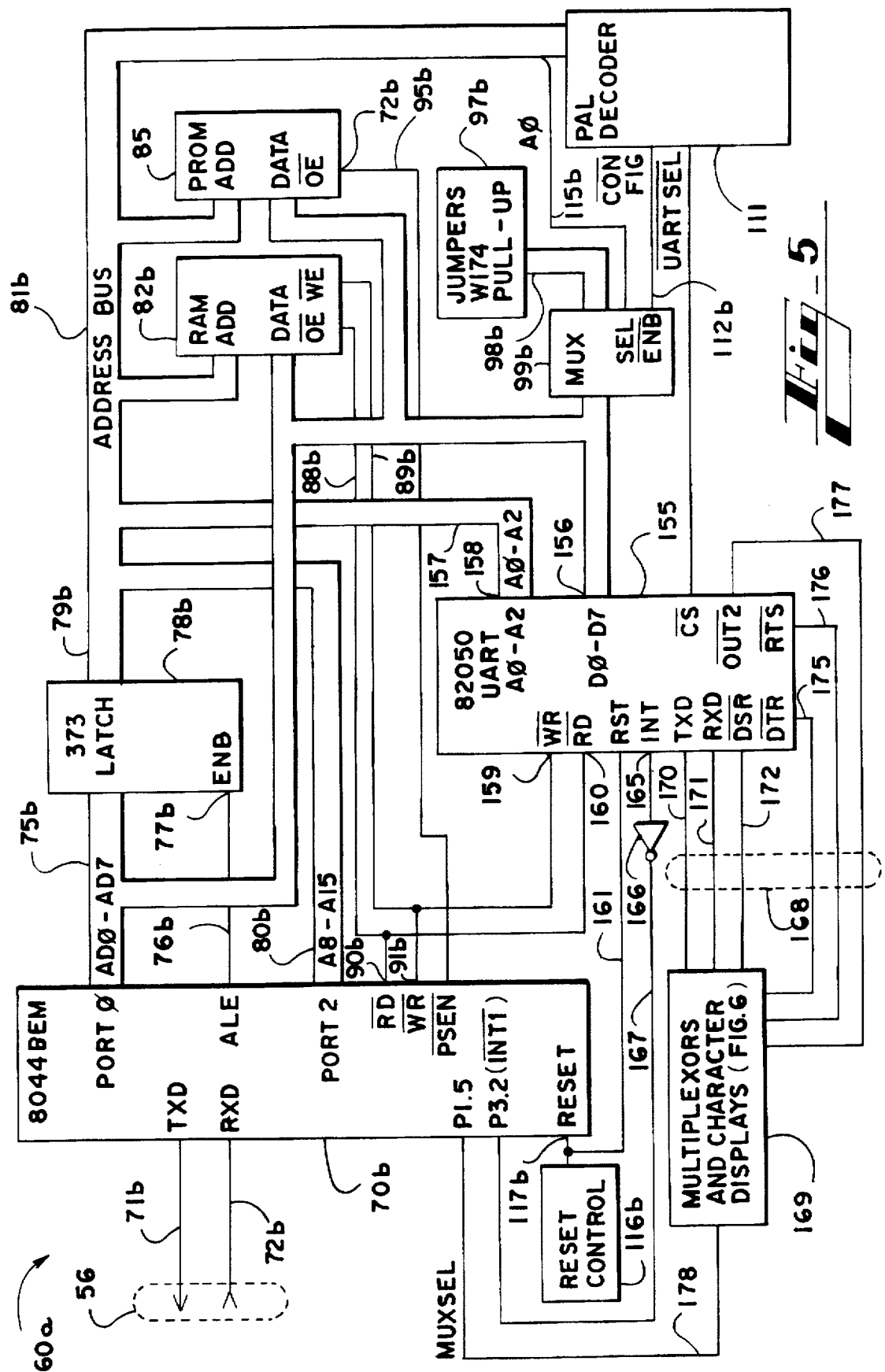
FIG. 5 is a partially schematic, partially block diagram of the multi-character display cluster controllers used in the preferred embodiment.

Before proceeding with the balance of the description of display and lights cluster controller 59a, it should be noted that the heretofore described structure of microcomputer 70a, its address latch 78a, the associated RAM, data buses and configuration jumpers, are identically reproduced in the display cluster controller 60a, shown in detail on FIG. 5. Thus, each element referenced by a numeral followed by a lower case "a" in this description of FIG. 3 has a corresponding numeral followed by a lower case "b" on the drawing of FIG. 5. These devices shown on FIG. 5 are identical to the corresponding devices shown on FIG. 3 and the description of the structure will not be repeated in connection with FIG. 5.

Continuing now with the description of the keyboard and lights controller 59a, the six lowest order bits of address bus 81a are tapped off to sub-bus 118 which is split into a sub-bus 119 carrying the three lowest order bits and sub-bus 120 carrying address bits A3–A5. Sub-bus 120 is decoded by a pair of type 138 three line to one-of-eight decoders 121 and 122. Decoder 121 is enabled by a negated I/O write signal (IOWR) on line 125 which is detected by PAL decoder 110. Similarly, an I/O read signal (IORD) appears on line 126 from PAL decoder 110. It should be noted that the outputs from read output 90a and write output 91a are provided along respective lines 127 and 128 as two of the inputs to PAL decoder 110. Thus, the higher order address lines, together with the read and write outputs from microcomputer 70a are decoded to address lamp write decoder 121 and switch read decoder 122.

The particular patient module whose lamps are to be written to is decoded by decoding address lines A3–A5 from sub-bus 120. When it is time to write to a particular lamp, line 125 goes active and one of the negated signals $WR_0$–$WR_7$, which appear on lines 129a–129h, respectively, goes active to select a lamp group of a particular patient tracking module. As is shown in FIG. 3, the first lamp group 62a and the first switch group 26a are collectively indicated as group 130a. The lamp and switch groups for other patient control modules controlled by cluster 59a are likewise connected to particular ones of lines 129b14 129h.

As will be explained in greater detail in connection with FIG. 4, the particular lamp or switch to be written to or read is encoded in the three lowest order address lines on sub-bus 119, which is provided to group 130a.

In a similar manner, the particular patient tracking module read lines $RD_0$–$RD_7$, which appear as lines 131a–131h, respectively, are activated in order to read the state of the switches of eight patient tracking modules which can be connected to cluster controller 59a. At this point, it should be noted that the preferred embodiment connected only seven patient control modules to each cluster controller in order to maintain symmetry in the 42 room facility for which it was designed. Thus, one of the lines 129 and one of the lines 131 will not be connected to a physical group in the preferred embodiment described herein. The additional inputs to group 130a include the reset signal on line 132 and an external data line which appears on line 135.

Figure 4:
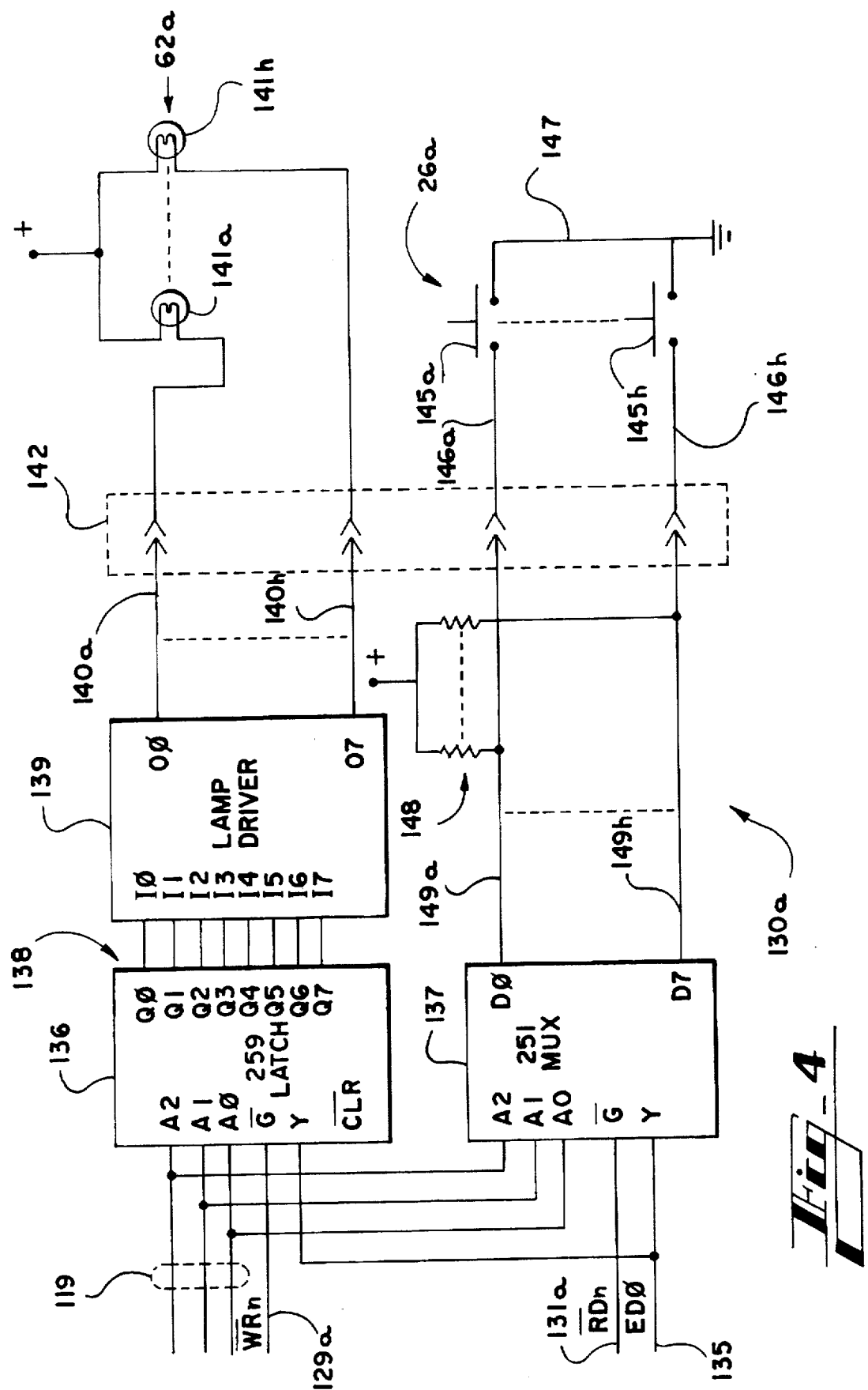
FIG. 4 is a schematic diagram of one set of order lamps, and order and entry keys of a particular patient tracking module that is controlled by the cluster controller shown in FIG. 3.

FIG. 4 shows a schematic diagram of group 130a. Sub-bus 119 carrying the three lowest order address lines are connected to the address inputs of a type 259 addressable latch 136 and a type 251 multiplexer 137. Turning first to the lamps, the single data line 135 is connected to the one line data input (Y) of addressable latch 136. The particular one of the eight latches contained within device 136 is selected by the state of sub-bus 119. When line 129a makes a low to high transition, the state of line 135 is latched on to the particular one of outputs 138 addressed by sub-bus 119. This drives one of the inputs to lamp driver 139 which has respective output lines 140a–140h. Lines 140 simply sink sufficient current to allow a particular one of lamps 141a–141h to be illuminated.

Again, it is noted that the designators in FIG. 4 show the possibility of driving eight lamps whereas only six are driven for each patient tracking module in the preferred embodiment.

It should be noted that lines 140 are connected to lamps 41 via a multi-conductor plug 142 that is designed to interface both switches 26a and lamps 62a to the cluster controller with which their patient module is associated.

The reading of the eight switches 145a–145h, which collectively form switch group 26a, is similar to the writing to the lamps. Switches 145 are single pole normally open momentary switches which, when closed, connect a respective one of lines 146 to ground on line 147. Pull-up resistors 148 pull lines 149 high when their associated switches 146 are open. A particular one of lines 149a–149h goes low when its associated switch closes.

Again, external data line ED0, which appears on line 135, carries the data back to the cluster controller. The multiplexer is enabled by the read group zero ($RD_0$) signal on line 131a and the particular one of lines 149a–149h that is connected to line 135 is determined by the state of sub-bus 119.

From viewing FIGS. 3 and 4 together, it should be apparent that up to eight duplications of the circuitry shown in FIG. 4 may be driven by the cluster controller illustrated in FIG. 3. In the preferred embodiment, seven such groups are driven by each cluster controller. Additionally, in the preferred embodiment six of the lamps 141 are used as order lamps behind order switches 27a (FIG. 1), although a greater or lesser number can be used in other embodiments of the present invention. In the preferred embodiment, all eight switches 145a-145h are used.

From inspection of FIG. 4, it will be apparent to those skilled in the art that there is no interrupt mechanism for detecting closure of one of switches 145. Indeed, none is used since microcomputer 70a of cluster controller 59a constantly polls the states of these switches. One of the tasks of the keyboard and light cluster controller 59a, which is controlled by the firmware in read only memory 84, is the debouncing of the signals on line 135 when switches 145 are read. Software debouncing routines are well known to those skilled in the art and same will not be described in detail herein.

It should be noted that keyboard controller 61 (FIG. 2), which handles input from alphanumeric keyboard 16a, is structurally identical to keyboard and lights cluster controller 59a shown in FIG. 3. In the interface to the keyboard, multiplexers similar to multiplexer 137 (FIG. 4) connect groups of the keyboard's keys together. The multiplexers are sequentially addressed by decoder 122 (FIG. 3). Since there are eight outputs of the decoder and three address lines provided on sub-bus 119, 64 keys may be serviced in this manner. From inspection of FIG. 1, it will be seen that keyboard 16a has only 39 keys and thus the adaptability of cluster controllers 59 to handle keyboard input will be appreciated by those skilled in the art.

Turning next to FIG. 5, the preferred embodiment of display cluster controller 60a is shown. As noted hereinabove, the display cluster controllers are also controlled by an Intel type 8044BEM one chip microcomputer shown as 70b in FIG. 5. Bitbus serial link 56 is connected to microcomputer 70b as is the case with the cluster controller shown in FIG. 3. Much of the conventional support circuitry, including latch 78b and RAM 82b and the like, is identical to that of the keyboard and lights cluster controllers 59. A PAL decoder 111 is used to decode particular signals used in the display cluster controller 60a. It is of the same type as PAL decoder 110 shown in FIG. 3 but implements different PAL equations.

Digressing for a moment, the displays 19 (FIGS. 1 and 2) used in the preferred embodiment are two line by 20 character vacuum fluorescent dot matrix displays. They communicate with the external devices via a four wire (plus ground) standard RS-232 interface. They are configured as RS-232 data communications equipment and their interface includes both the transmit and receive data lines and a clear to send (CTS) input line and a data set ready (DSR) output line. This being the case, the display cluster controllers 60a communicate with these devices through a universal asynchronous receiver transmitter (UART) 155 shown in FIG. 5.

In the preferred embodiment, a type 82050 UART is used. Since UARTs are relatively expensive devices and multiplexers are relatively inexpensive, and because cluster controller 60a sequentially services the displays 19 of the patient tracking modules associated with its cluster, the connections to UART 155 are multiplexed among the seven multi-character displays 19 associated with the cluster. Data bus 75b is connected to the parallel data port 156 of UART 155. A three line sub-bus 157 brings the three lowest order address bits to address inputs 158 of the UART. It is well known to those skilled in the art that the signal state on these inputs controls the reading from and writing to particular registers within the UART in a well known and documented manner. The negated write and read inputs 159 and 160 are connected to the corresponding outputs 91b and 90b of microcomputer 70b. A reset signal is provided on line 161 from reset controller 116b that initializes UART 155 when a reset of microcomputer 70b occurs. An interrupt output 165 is inverted by inverter 166 and provides an active low signal on line 167 which is connected to pin 2 of port 3 of microcomputer 70b. This pin is configured as a hardware interrupt pin for a microcomputer. This is used to generate a hardware interrupt to the processor to indicate that a byte has been received and needs to be read by microcomputer 70b and stored in an appropriate location in random access memory 82b for further processing. In the preferred embodiment, this is only used to receive acknowledgements which are transmitted by the devices embodying displays 19 in the preferred embodiment.

A collection of six lines, surrounded by dashed line 168 in FIG. 5, is connected between UART 155 and a block 169 that includes all of the multiplexers and multi-character displays associated with this particular cluster. The contents of block 169 are shown in detail in FIG. 6. The collection of lines 168 consists of the transmit and receive data lines 170 and 171 from UART 155, the data set ready input line 172, the data terminal ready and request to send outputs 175 and 176, and line 177 which carries the OUT2 output from UART 155. Those skilled in the art know that this output can be controlled via the internal registers of the UART by writing particular words to these registers. Additionally, a signal bearing the mnemonic MUXSEL is provided on line 178 from pin 5 of port 1 of microcomputer 70b to multiplexers and character displays box 169.

Figure 6:
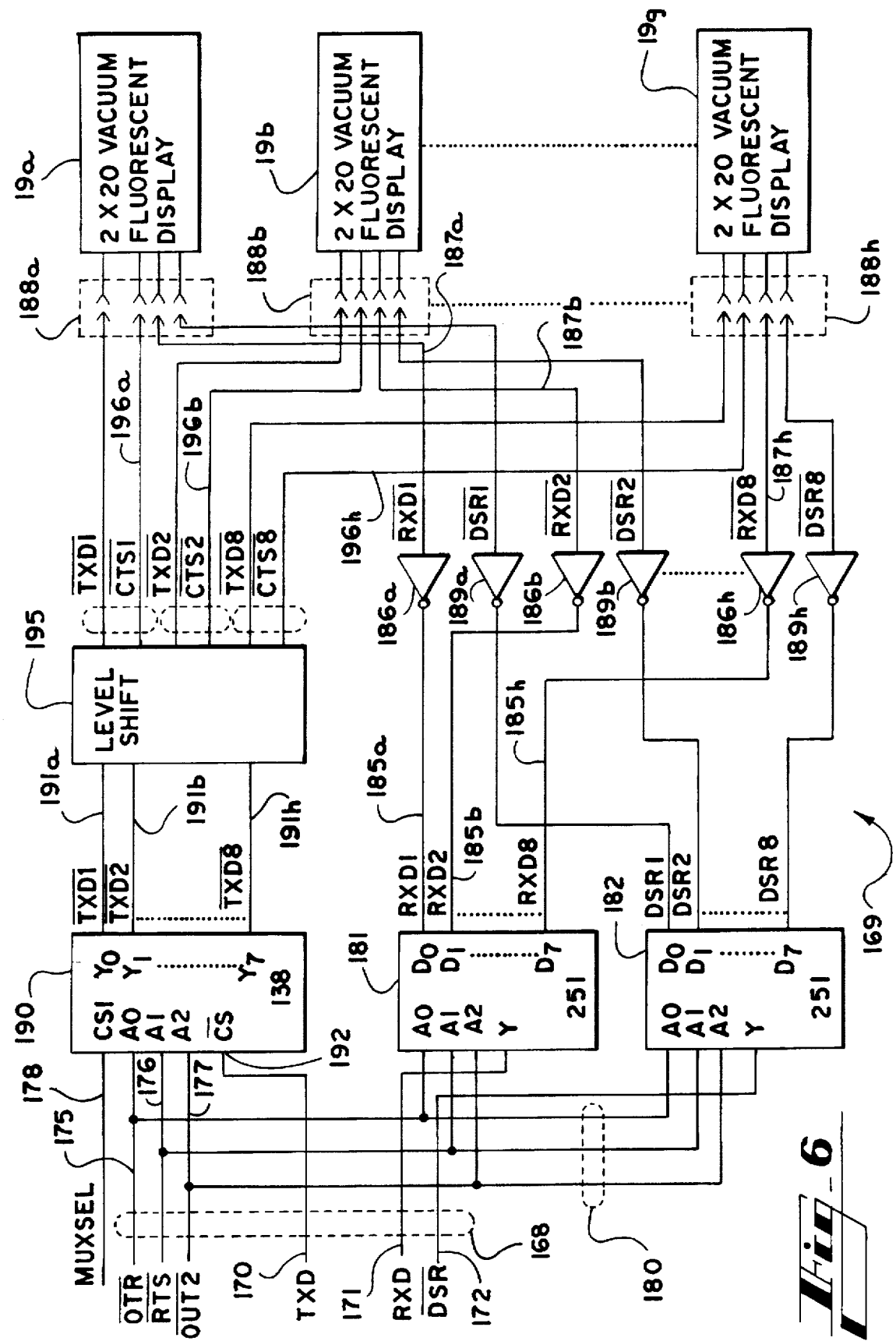
FIG. 6 is a schematic diagram of a cluster of multi-character displays controlled by the cluster controller of FIG. 5.

Turning next to FIG. 6, the apparatus within block 169 and the interconnections of the lines connected thereto is shown. Lines 175-177 are collectively labeled by dashed line 180 and form a three line address bus that selects a particular one of eight possible displays 19 to be connected to UART 155 (FIG. 5). Again, only seven displays 19a-19g are used in each cluster of the preferred embodiment so it should be understood that one of the sets of output lines in the preferred embodiment is not used. The outputs from the vacuum fluorescent display devices 19 to the UART are connected through multiplexers 181 and 182. These multiplexers carry, respectively, the receive data signals coming from the vacuum displays to the UART and the data set ready (DSR) status lines. Multiplexers 181 and 182 are preferably embodied by type 251 8-to-1 multiplexers which are well known to those skilled in the art.

Turning for a moment to the receive data lines, the eight receive data lines RXD1-RXD8 appear on lines 185a-185h. These signals are the outputs of inverting level shifters 186a-186h. The inputs to these level shifting inverters appear respectively on lines 187a-187h. Level shifting inverters 186 shift the logical receive data signals from their 12 volt level used on a standard RS-232 interface to the 5 volt TTL level that appears on lines 185. These lines are connected through plugs 188a-188h into which the vacuum fluorescent displays 19a-19g are, respectively, connected. Of course one of the plugs does not have a display device connected thereto since only seven displays are used in each cluster. An identical arrangement is used for the RS-232 level data set ready signals from each of the plugs 188 that are passed through a similar set of level shifting inverters 189a-189h to provide inputs to multiplexer 182.

On the transmit data side, an active state on the MUXSEL line 178 conditions three line to one-of-eight decoder 190 to activate a particular one of its outputs, which appear on lines 191a–191h. Since the input transmit data line 170 is connected to an inverted chip select input 192, decoder 190 acts as an inverter. Lines 191a–191h are provided to a level shifting circuit 195 which also provides a network for holding clear to send lines 196a–196h active. Therefore, the three UART outputs that appear as a small address bus 180 cause decoder 190 to select a particular one of the transmit data lines 191 to be connected through level shifter 195 to transmit data to the input of the RS-232 interface of one of vacuum fluorescent displays 19. Therefore, viewing FIGS. 5 and 6 together it will be appreciated that display cluster controllers can selectively service the individual multi-character displays 19 by multiplexing the connections between the RS-232 ports of these displays and UART 155 (FIG. 6).

Next, the operation of the three major firmware components of the patient tracking system of the preferred embodiment will now be described. The routines described herein will be appreciated by those skilled in the art and it was not believed that flow charts would be particularly useful in assisting in the understanding of same.

The three main components are the firmware driving central controller 40 which is stored in the read only memories of memory circuits 42 (FIG. 2), the keyboard and lights cluster controller firmware stored in programmable read only memory 84, (FIG. 3) and the display cluster controller firmware stored in read only memory 85 (FIG. 5).

Working somewhat backwards, from the cluster controllers back to the central controller, the operation of these devices will now be described. Except in the event of a device failure, display cluster controllers 60 have very little to say to central controller 40. The firmware driving these cluster controllers simply monitors the data stream on Bitbus serial link 56 for packets that are addressed to it, i.e., having an address corresponding to the setting of some of jumpers 97b. When a packet is received, address information within the packet is further decoded to determine the particular one of the displays 19 of the cluster for which the data is intended. Additionally, a simple command syntax has been defined by the inventors of the present invention for instructing the cluster controllers to write to particular ones of the four fields 20a–22a and 25a illustrated in FIG. 1. The commands include commands to write to each field, to set a blink characteristic for each field, and to control the intensity of the output of the display. The firmware of the cluster controller generates the signals required by the displays to effect writing to particular fields. The firmware in read only memory 85 controls decoding and storage of textual data in ASCII code in RAM 86b for writing via UART 155 to a particular selected one of the displays. The display cluster controller monitors the receive data line from the RS-232 port of the display being written to for acknowledgements. If desired, the vacuum fluorescent display devices will send back the contents of their memory buffers although this task is not normally performed as part of the routine operation of the preferred embodiment.

The firmware of the display cluster controller also runs a task in the background to make sure it receives acknowledgements from each attached display device when an appropriate signal is sent to the display. If one of the displays is not responding, the firmware of the display cluster controller will take the device off line and ignore subsequent commands from the central controller to write data to this device, while regularly attempting to reestablish communication. The cluster controller also stores an error list when it detects a malfunction in a display and transmits this information back to the central controller the next time it receives a communication from the central controller.

Since a need to write to the displays 19 only arises when patient identification or physician or nurse designators need to be written or modified in the display, or some change in brightness or the like needs to be effected, the central processor occasionally (approximately once every 30 seconds) polls the display cluster controllers even if it has no data to send them in order to receive any error messages that may be generated by the cluster controllers. Since the Bitbus protocol is a subset of the IBM synchronous data link control (SDLC) standard, the cluster controllers are slave controllers and can only speak when spoken to in the architecture of the system.

Turning next to the keyboard and lights controllers 59, it has already been mentioned that the firmware in read only memory 84 performs a software debounce of operation of switches 145a–145h. Once debouncing has been performed, and the firmware has determined that a switch closure has occurred, a record of this event is stored in RAM 82 for communication back to the central controller the next time the cluster controller 59 is polled.

The firmware of the cluster controllers 59 also controls the states of lamps 141 (FIG. 4). The current system state for each of the lamps can only be established by a command from central controller 40. The current system state of the lamps is stored in random access memory 82a. There are four system states for each lamp: OFF, ON, SLOW FLASH, and FAST FLASH. The cluster controllers 59 internally control implementation of these states. One of the internal timer counters of microcomputer 70a is used to generate a blink clock signal for the fast flashing state and multiple transitions of this clock establish the cadence for the slow flash. The firmware regularly writes the lamp status for each lamp out to the latches driving same for each patient tracking module. The status for each particular lamp is checked from a table in RAM and 1 or 0 is written according to whether the lamp is on or off.

For lamps in a flashing state, the system checks the current state of a status register that indicates whether the blinking signals should be on or off at that time and writes the appropriate bit to that particular flashing lamp. It should be noted in connection with the flashing status that, as previously described, the flashing of lamps in a patient tracking module connected to one cluster controller are asynchronous to the flashing of lamps in patient modules connected to other cluster controllers since the flash cadence is generated locally at each cluster controller. Since it is considered undesirable and distracting to have such asynchronous flashing of lamps at a nurses station, the preferred embodiment provides a synchronized flash command that is generated in rapid sequence to all keyboard and lamp cluster controllers to restart the blink clocks. This resynchronizes the flashing characteristics of all flashing lamps as viewed by an observer.

Whenever one of cluster controllers 59 receives a command from central controller 40 over serial link 56, and it has stored the operation of one or more keys, it sends back a packet to the central controller indicating the identity of the particular key that was operated. In order that there not be an undesirably long time between user operation of the key and the manifestation of this by a change of its associated lamp state, the central controller polls each of the cluster controllers approximately once every 50 milliseconds. This takes us back to the central controller 40. The firmware associated with the central controller has the following tasks. It periodically polls each of the keyboard and lights cluster controllers 59 as described hereinabove. It sends status information as to what the status of particular lamps and particular patient tracking modules should be. It also accepts replies indicating the identity of a particular key that has been operated. It also polls keyboard console controller 61 at approximately the same rate.

The memory 42 of the central controller contains a table that associates particular physical room numbers with particular patient tracking modules of particular clusters. These can be reconfigured as needed. In the preferred embodiment, the physical location of the patient tracking module should correspond to a particular physical location in the hospital and thus, the top patient tracking module on the left hand side of the panel shown in FIG. 1 should be understood by hospital personnel to identify the patient in a particular physical room in the hospital.

An example of entry via console keyboard 16a of patient information identifiers will serve to describe how information is transmitted from console keyboard 16a to the display 19 associated with a particular one of the patient tracking modules for which it is intended. Assume that a particular patient has been assigned to a particular room. In the preferred embodiment as currently constructed, patient name and patient complaint fields 20 and 21 are provided through serial link 48 from hospital host computer 49. Next assume that hospital personnel at the nursing station where the patient tracking system resides want to enter a designation of the doctor's initials or a number code corresponding to the responsible physician. First, key 36 is depressed. Operation of this key is detected during a polling of console keyboard 16 by its associated keyboard console controller 61 and stored in the controller's memory. Continuing with the example, assume that the keys corresponding to the letters JBB, i.e., the physician's initials, are operated next. The operation of each key is detected, debounced, and stored in the memory of the controller.

In the meantime, central controller 40 has been routinely polling controller 61 and has received messages indicating operation of each of these keys. Data concerning the particular keystroke sequence is buffered in the memory 42 of the central controller.

Each time keyboard console controller 61 sends a reply indicating that it has detected a keystroke, a retriggerable timer is restarted in central controller 40. It will continue to buffer the characters unless and until this timer times out or the operation of an enter key is reported by one of the keyboard and light cluster controllers 59. When operation of an enter key at a particular patient tracking module is detected, central controller 40 checks its character buffer in which it stores characters corresponding to keystrokes from console keyboard 16. A check of message length and validity is made. At this point, if the hospital has implemented any coding to identify nurses or doctors, such as assignment of an employee number or the like, which needs to be translated into initials, this translation takes place.

Assume that operation of an enter key at a particular patient tracking module is detected before the timeout of the timer, and that the buffered data indicates a valid command to write to a particular field of one of the multi-character displays 19. The central controller then assembles a packet directed to the particular one of patient tracking modules 15 that reported operation of its enter key. This packet is addressed to the display controller for the cluster of which that patient tracking module is a member. Continuing with the example, the packet will instruct the display controller to route data "JBB" to the physician identification field 22 of that particular display since MD key 36 was depressed as part of the keystroke sequence.

While it is not currently performed in the preferred embodiment, it will be apparent to those skilled in the art that additional dedicated keys such as keys 35 and 36 could be provided for patient name flags and patient complaint flags. Alternately, minor modifications to the firmware controlling the central controller could be made so that multiple operations of the enter key within a time window could signify a field designator for the buffered string of keystrokes stored in the memory of central controller 40.

Next consider an example where a particular one of order keys 27 is depressed in order to turn on its associated order lamp. As described hereinabove, the firmware with the keyboard and lights cluster controller detects operation of the key and reports this back to the central controller the next time the cluster controller is polled. The firmware controlling the central controller updates a status list it maintains for all lamps of the system indicating that the particular associated order lamps should be turned on. Additionally, it generates a packet for the next time it communicates with that particular cluster controller, which includes an instruction to turn the particular associated lamp on. When this command is received by the cluster controller it writes an appropriate bit to the particular one of addressable latches 136 (FIG. 4) associated with a particular lamp and thus causes the lamp to become illuminated. Since each of the keyboard and lamp cluster controllers is polled approximately 20 times a second, there is only a fraction of a second delay between the time the key is operated and the lamp comes on.

In addition to generating the packet to communicate with the cluster controller, the central controller will also set a bit in hex I/O array 50 to turn on the corresponding lamp in the patient's room. Likewise, if it is operation of a key in one of the rooms that is detected via one of lines 55, the same packet will be sent to a cluster controller having the patient module associated with that room, and the same bit will be set in hex I/O array 50 to turn on the lamp in the room.

While in the preferred embodiment the lamps and switches connected to lines 52 and 55 duplicate the functions of the lamps and switches in the patient tracking modules, it may be readily seen that a change in firmware can be made in order to cause the system not to recognize certain commands to change the status of an order lamp that are generated at a patient's room. Also, if it was ever desired to use one of the lamps as a call lamp to the nurse's station it would be possible to configure a system, making only firmware changes, which assured that the call lamp could only be turned off at the patient's room thus, preventing nursing personnel from clearing the call lamp at the station without attending to the patient.

As noted hereinabove, the preferred embodiment establishes one or more predetermined times as the maximum time it should take to execute an order. While these are programmable and selectable by the hospital, and can be varied as circumstances dictate, the preferred embodiment establishes 15 minutes as the maximum time for all orders except an order for services of the radiology department for which a 20 minute period is established.

Central controller 40 maintains the status of all these timers. It will be quickly appreciated that this creates the possibility of numerous timers which could be difficult to service in an efficient manner. The preferred embodiment addresses this in the following fashion. Each time a lamp is turned on an entry for this lamp is added to a linked list. The list includes an entry identifying the lamp and the particular patient module, and numerical value indicating the number of seconds difference between the time this timer should time out and the time the next shortest timer above it in the linked list will time out. This is obtained by checking the current remaining time on the current shortest timer and adding the time differences for sequential members of the list until the system detects the two entries between which the timeout period for the current one falls or the fact that the new entry should be at the bottom of the list. A difference value is then computed for the new entry and the member above it in the list, and it is added to the linked list. Central controller 40 generates a one second tick clock, which in turn generates a software interrupt that services the order timeout routine. This simply decrements the current value of the top member of the list by one second and then returns control to the main polling loop for the central controller.

First consider the example of when the member at the top of the list times out, i.e., when its count value is decremented to zero and the central controller does not receive an indication that the associated order switch was operated indicating execution of the order. When this event is detected the central controller assembles a packet for the appropriate cluster controller instructing it to set the appropriate lamp to its slow flash state. It next generates an entry for the table indicating the timeout period for the next change of state which will be a transition to fast flash. This entry is then added to the table as described hereinabove.

The next member of the linked list now becomes the top member and its value begins to be decremented by the one second tick counter. Since the numerical value of this entry was simply the number of seconds difference between its timeout and the timeout of the previous timer, the system need only commence decrementing this value in order to maintain the integrity of the timed periods. This continues until the entire list is exhausted.

Naturally, whenever operation of a key is detected and the change in the lamp status table indicates that a lamp is being turned off, the linked list of timers is scanned to remove any list entries that were associated with the extinguished lamp.

Next consider the example where the order is executed in a timely fashion. Under these circumstances the scan of the table indicate that the current top member of the linked list is the one to be removed. When this occurs, the current value of the timer of the removed top member simply added to the value of the next member of the list and this augmented value becomes the top member of the list, and begins being decremented by the tick clock. Thus, the integrity of the relationship of all entries is maintained without having to individually service each timer upon each interrupt.

Lastly, the ease with which personnel may transfer the electronic patient chart from one patient tracking module to another will be described. As noted hereinabove, one of the two non-illuminated keys 28 is an enter key that is used to indicate the particular patient tracking module in which patient, physician or nurse identifiers entered at console keyboard 16 should be stored. The other non-illuminated key is a MOVE key. This allows the electronic patient chart from one patient tracking module to be transferred to another patient tracking module to correspond to movement of the patient between two physical locations in the hospital. This is accomplished by depressing the dedicated move key at the patient tracking module associated with the patient's current room followed by depression of the move key of the patient tracking module of the destination room within a predetermined period of time, five seconds in the preferred embodiment. From the foregoing, the handling of this by the central controller should be readily appreciated. Detection of the move key is reported by the cluster controller when next polled. The central controller 40 detects operation of a move key and sets a flag. Each time operation of a move key is detected the status of this flag is checked. If the flag is still set, a set of packets is generated that cause all of the data to be transferred from the current room to the destination room. It also causes clearing of data from the patient tracking module associated with the current room.

Naturally, if the timer times out, the flag is cleared so that only intentional moves indicated by sequential operations of move keys within a relatively short period of time will cause the data to actually be transferred. Whenever a move takes place, the linked list of timers is also scanned and if a entry is found for the previous room, it is simply modified to reflect the new destination room. Thus, all of the data as well as timer status for the order timers is transferred whenever a move operation takes place.

From the foregoing it will be appreciated that the preferred embodiment of the present invention indeed meets the objects described hereinabove. It effectively implements an electronic patient chart. The order keys provide a simple but strong color coded visual indication of physician orders which need to be fulfilled. The system automatically establishes alarm limits for the time for fulfilling these orders and changes the indicator status if an associated order timer times out. It provides for entry of data either at a local keyboard console or via a serial communication link using a simple command syntax to the central controller which allows strings of ASCII coded data to control the status of the displays and lamps. While the preferred form of the present invention is one that employs a master/slave architecture in which the central controller is the master and the cluster controllers are the slaves, it will be appreciated that the overall functional result of implementation of the electronic chart is what gives the present invention its value. Therefore, the scope of the present invention should not be limited by particular details of the preferred embodiment but only by the claims below and equivalents thereof.

What is claimed is:

1. A hospital patient tracking system comprising in combination:
 a plurality of clusters of patient tracking modules, each said patient tracking module comprising:
  (a) a predetermined number of coded selectively operable keys each corresponding to a predetermined physician order,
  (b) a predetermined number of selectively operable visual indicators associated on a one-to-one basis with said coded selectively operable keys, and
  (c) a multi-character display;
 a plurality of keyboard cluster controllers, each said keyboard cluster controller being connected to said coded selectively operable keys and said selectively operable visual indicators and all of said patient tracking modules within associated cluster;
 a like plurality of visual indicator cluster controllers, each said visual indicator cluster controller being connected to said coded selectively operable keys and said selectively operable visual indicators in all of said patient tracking modules within an associated cluster;
 a like plurality of multi-character display cluster controllers, each said multicharacter display cluster controller being connected to said multi-character display in all of said patient tracking modules within an associated cluster;

at least one console keyboard and an associated console keyboard controller in each said cluster; and a central controller in each said cluster connected to each one of said keyboard and visual indicator cluster controllers, each one of said multi-character display cluster controllers, and said console keyboard controller for providing data to, and receiving data from said cluster controllers and said console keyboard controller said central controller including a memory for storing a plurality of patient identifiers and for associating each particular one of said patient identifiers with a particular one of said patient tracking modules within a particular one of said plurality of clusters;

wherein said keyboard and visual indicator cluster controllers are responsive to operation of a particular one of said coded selectively operable keys to buffer and store a key activation packet that is passed on to said controller in response to a polling request from said central controller to the particular said keyboard and visual indicator cluster controller to which said particular one of said coded selectively operable keys is connected, wherein said central controller is responsive to receipt of said key activation packet to generate an indicator control packet that is sent to said particular keyboard and visual indicator cluster controller, and wherein said particular keyboard and visual indicator cluster controller is responsive to said indicator control packet to cause the particular selectively operable visual indicator associated with said particular one of said coded selectively operable keys to change states.

2. A hospital patient tracking system as recited in claim 1 wherein:

said central controller further comprises timing means for detecting the passage of a predetermined period of time since a last state change for said particular selectively operable visual indicator and said central controller is responsive to said timing means detecting said passage of said predetermined period of time to place said particular selectively operable visual indicator in an alarm state.

3. A hospital patient tracking system comprising in combination:

a plurality of clusters of patient tracking modules, each said cluster comprising a rectilinear array of said patient tracking modules, each said patient tracking module comprising:

(a) a predetermined number of coded selectively operable keys arranged in a row, (b) a predetermined number of selectively operable visual indicators being associated with and physically juxtaposed on a one-to-one basis with said coded selectively operable keys, (c) a multi-character display disposed by said row;

a like plurality of cluster controllers, each said cluster controller being connected to said coded selectively operable keys and said selectively operable visual indicators and said multi-character display in all of said patient tracking modules within an associated cluster;

at least one console keyboard and an associated console keyboard controller connected thereto;

a central controller connected to each one of said cluster controllers, and said console keyboard controller for providing data to, and receiving data from said cluster controllers and said console keyboard controller, said central controller including a memory for storing a plurality of patient identifiers and for associating each particular one of said patient identifiers with a particular one of said patient tracking modules within a particular one of said plurality of clusters.

4. A hospital patient tracking system as recited in claim 3 wherein said predetermined number is a first predetermined number and wherein each said patient tracking module further comprises:

a second predetermined number of function keys connected to a particular one of said plurality of cluster controllers associated with the cluster of which said patient tracking module is a member.

* * * * *